(12) United States Patent
Nose et al.

(10) Patent No.: US 6,385,481 B2
(45) Date of Patent: *May 7, 2002

(54) DIAGNOSTIC SYSTEM WITH A CHAIR AND TABLE MOVABLE ON RAILS PROVIDED ON VERTICAL MAGNETS THEREOF

(75) Inventors: Katsumasa Nose; Osamu Furuta; Kazuhiko Hayakawa; Masaaki Sakuma; Yujiro Hayashi, all of Tokyo (JP)

(73) Assignee: GE Yokogawa Medical Systems, Limited, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/218,402

(22) Filed: Dec. 22, 1998

(30) Foreign Application Priority Data

Jan. 28, 1998 (JP) .............................................. 10-015829

(51) Int. Cl.[7] .............................................. A61B 5/055
(52) U.S. Cl. ................................. 600/415; 5/601; 5/611
(58) Field of Search ................................. 600/410, 415, 600/421, 422; 324/318–319, 322; 5/601, 611, 620

(56) References Cited

U.S. PATENT DOCUMENTS 4,805,626 A * 2/1989 DiMassimo et al. ......... 600/415
5,042,487 A * 8/1991 Marquardt ................... 600/425
6,011,396 A * 1/2000 Eckels et al. ................ 600/415

FOREIGN PATENT DOCUMENTS

| DE | 3909276 | 10/1989 |
| EP | 0121367 | 10/1984 |
| EP | 0712606 | 5/1996 |
| JP | 62197309 | 12/1987 |
| JP | 3205029 | 9/1991 |
| JP | 5161623 | 6/1993 |
| JP | 9024018 | 1/1997 |
| JP | 10295665 | 11/1998 |

* cited by examiner

Primary Examiner—Ruth S. Smith
(74) Attorney, Agent, or Firm—Moonray Kojima

(57) ABSTRACT

The present invention is directed to joint motion imaging and provides a vertical magnet type MRI system comprising a vertical magnet unit (10) having a pair of opposite vertical magnets (11), a movable table (20) provided with wheels (22) for traveling and a cradle (21) to carry a specimen laid down thereon, and capable of being moved into and moved out of a space between the pair of opposite vertical magnets (11), table locking devices (13) for locking the movable table (20) with the cradle (21) being in place between the pair of opposite vertical magnets (11), a movable chair (30) provided with wheels (32) for traveling and capable of being moved into and moved out of the space between the pair of opposite vertical magnets (11), and a chair locking device (14) for locking the movable chair (30) in place between the pair of opposite vertical magnets (11).

10 Claims, 6 Drawing Sheets

DIAGNOSTIC SYSTEM WITH A CHAIR AND TABLE MOVABLE ON RAILS PROVIDED ON VERTICAL MAGNETS THEREOF

BACKGROUND OF THE INVENTION

The present invention relates to a MRI system (magnetic resonance imaging system) and a movable table. More particularly, the present invention relates to a MRI system and a movable table capable of properly dealing with joint motion imaging.

A conventional MRI system employs a stationary table integrally combined with a magnetic unit. A specimen, i.e., a patient, is laid down on the stationary table for the production of images of the specimen. The stationary table, however, makes joint motion image production, i.e., kinematic image production, in which images of a joint in different angular positions are produced, difficult.

SUMMARY OF THE INVENTION

Accordingly, it is an object of the present invention to provide a MRI system suitable for joint motion imaging.

According to a first aspect of the present invention, a MRI system comprises a vertical magnet means having a pair of vertical magnets having opposite vertical surfaces, and a wheeled movable chair capable of entering a space between the pair of opposite vertical magnets with a specimen seated thereon.

The insertion of the movable chair carrying a specimen seated thereon into a magnetic unit facilitates joint motion image production. However, it is difficult to send the movable chair carrying a specimen seated thereon into the magnet unit of a cylindrical magnet MRI system provided with a cylindrical magnet or a horizontal magnet MRI system provided with a pair of horizontal magnets respectively having opposite horizontal surfaces, because part of the magnet lies between a magnet center, i.e., a position where the intensity of a gradient magnetic field is naught, and the surface of the floor.

The MRI system of the present invention employs a vertical magnet unit having a pair of opposite vertical magnets, and a movable chair capable of entering a space between the pair of opposite vertical magnets. Any part of the magnet does not lie between the magnet center and the surface of the floor in the vertical magnet type MRI system provided with a pair of vertical magnets having opposite vertical surfaces. Therefore, the movable chair carrying a specimen seated thereon can be moved to the magnet center, so that joint motion imaging can properly be achieved.

According to a second aspect of the present invention, the foregoing MRI system further comprises a chair locking means capable of locking the movable chair positioned in the space between the pair of opposite vertical magnets of the vertical magnet means.

The chair locking means may be provided only at the opposite vertical magnet side, only at the movable chair side or at both the opposite vertical magnet side and the movable chair side.

According to a third aspect of the present invention, a MRI system comprises a vertical magnet means having a pair of vertical magnets having opposite vertical surfaces, a wheeled movable table capable of carrying a cradle in which a specimen is laid down into and out from a space between the pair of opposite vertical magnets, a table locking means for locking the table positioned in the space between the pair of opposite vertical magnets of the vertical magnet means, a wheeled movable chair capable of entering a space between the pair of opposite vertical magnets with a specimen seated thereon, and a chair locking means capable of locking the movable chair positioned in the space between the pair of opposite vertical magnets of the vertical magnet means.

Joint motion imaging can satisfactorily be achieved if a specimen held in a sitting position on a chair can be sent into the magnet unit. However, it is difficult to send the specimen held on a chair in a sitting position into the magnet unit of a cylindrical magnet MRI system provided with a cylindrical magnet, or a horizontal magnet MRI system provided with a pair of horizontal magnets respectively having opposite horizontal surfaces, because part of the magnet lies between a magnet center, i.e., a position where the intensity of a gradient magnetic field is naught, and the surface of the floor. In the vertical magnet type MRI system provided with a pair of opposite vertical magnets respectively having opposite vertical surfaces, any part of the magnets does not lie between the magnet center and the surface of the floor. However, a specimen held on a chair in a sitting position cannot be sent into the magnet unit because a stationary table interferes with the chair.

A MRI system of the present invention employs a vertical magnet unit having a pair of opposite vertical magnets, a movable table, and a movable chair.

In a vertical magnet type MRI system, no magnet lies between a magnet center, i.e., a point C in FIG. 2, and the surface of the floor, i.e., a surface F in FIG. 2. The movable table can easily be removed from the magnet unit. Therefore, the movable chair holding a specimen in a sitting position thereon can be moved to the magnet center after removing the movable table from the magnet unit. Thus, joint motion imaging can satisfactorily be achieved.

The table locking means may provided only at the opposite vertical magnet side, only at the movable table side or at both the opposite vertical magnet side and the movable table side. The chair locking means may provided only at the opposite vertical magnet side, only at the movable chair side or at both the opposite vertical magnet side and the movable chair side.

According to a fourth aspect of the present invention, in the MRI system according to any one of the first to the third aspect of the present invention, the movable chair is used for the joint motion imaging of the lumbar region or the neck region.

The medical examination of the lumbar and the cervical vertebrae can satisfactorily be achieved by carrying out joint motion imaging while the lumbar and the cervical vertebrae are moved under load.

According to a fifth aspect of the present invention, a movable table for horizontally moving a cradle in which a specimen is laid down by electric power, comprising wheels, and a power receiving means for receiving electric power for driving the cradle for horizontal movement from a gantry.

Since electric power for driving the cradle for horizontal movement is received from the gantry, the movable table need not be loaded with heavy batteries and can lightly be moved.

Work for laying a patient down on a stationary table in a place in which it is difficult to carry out such work, such as a place where the MRI system is installed, will make the burden too heavy for the patient and the technicians. Since the MRI system cannot be operated during work for laying the patient down on the stationary table, the rate of operation of the MRI system is reduced.

When the MRI system and the movable table of the present invention are used, a specimen laid down on the movable table or the movable chair at some other place can be transported to and can be sent into the magnet unit. Therefore, specimen transferring work is unnecessary, which reduces burden on the patient and the technicians. Since the specimen can quickly be changed, downtime during which the MRI system is stopped can be shortened and the rate of operation of the MRI system is increased.

The MRI system according to the present invention enables the specimen to be carried in a sitting position to the magnet center and is able to deal properly with joint motion imaging.

The movable table according to the present invention receives electric power for driving the cradle for horizontal movement from the gantry. Therefore, the movable table need not be loaded with heavy batteries and can lightly be moved.

Further objects and advantages of the present invention will be apparent from the following description of the preferred embodiments of the invention as illustrated in the accompanying drawings.

DETAILED DESCRIPTION OF THE INVENTION

A preferred embodiment of the present invention will be described in detail with reference to the accompanying drawings.

Figure 1:
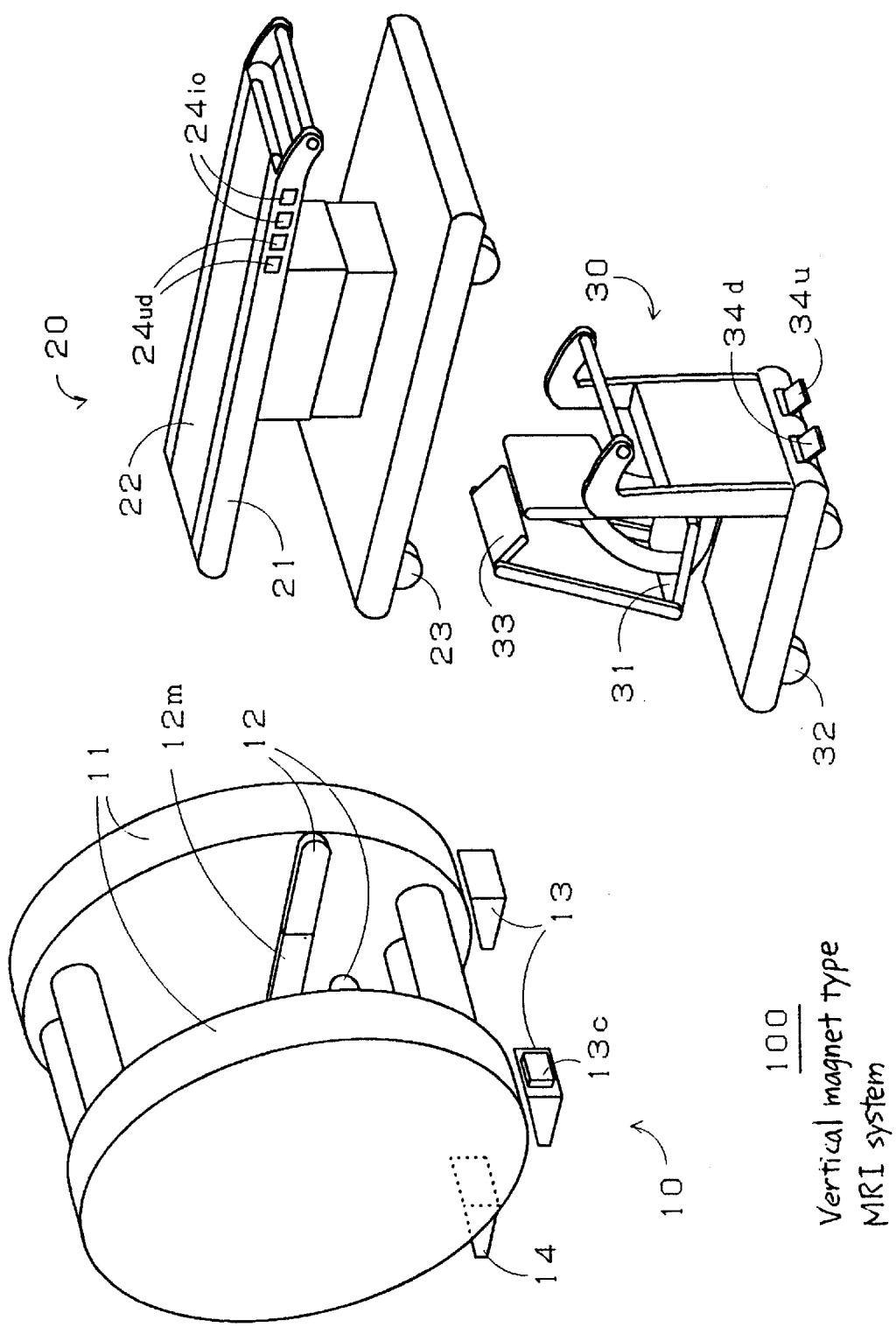
FIG. 1 is a typical perspective view of a vertical magnet type MRI system in a preferred embodiment according to the present invention.

FIG. 1 is a perspective view of a vertical magnet type MRI system 100 in a preferred embodiment according to the present invention.

The vertical magnet type MRI system 100 comprises a vertical magnet unit 10, a movable table 20 and a movable chair 30.

The vertical magnet unit 10 comprises a pair of vertical magnets 11 disposed opposite to each other with their vertical surfaces facing each other, nonmagnetic rails 12, table locking devices 13, and a chair locking device 14. Each of the rails 12 has a removable middle section of about 12m. One of the table locking devices 13 is provided with a power feeder connector 13c for electrically connecting the movable table 20 to the table locking device 13.

The movable table 20 comprises a table top 21 capable of being vertically moved by a hydraulic mechanism, a nonmagnetic cradle 22 supported on the table top 21 and capable of being horizontally moved by a motor, wheels 23 for traveling, up/down buttons 24ud to be operated to move the table top 21 vertically, and in/out buttons 24io to be operated to move the cradle 22 horizontally forward and backward relative to the table top 21.

The movable chair 30 comprises a nonmagnetic seat 31 capable of being vertically moved by a hydraulic mechanism, wheels 32 for traveling, a foldable footrest 33, a raising pedal 34u to be operated to raise the seat 31 by the hydraulic mechanism, and a lowering pedal 34d to be operated to lower the seat 31 by the hydraulic mechanism.

Figure 2:
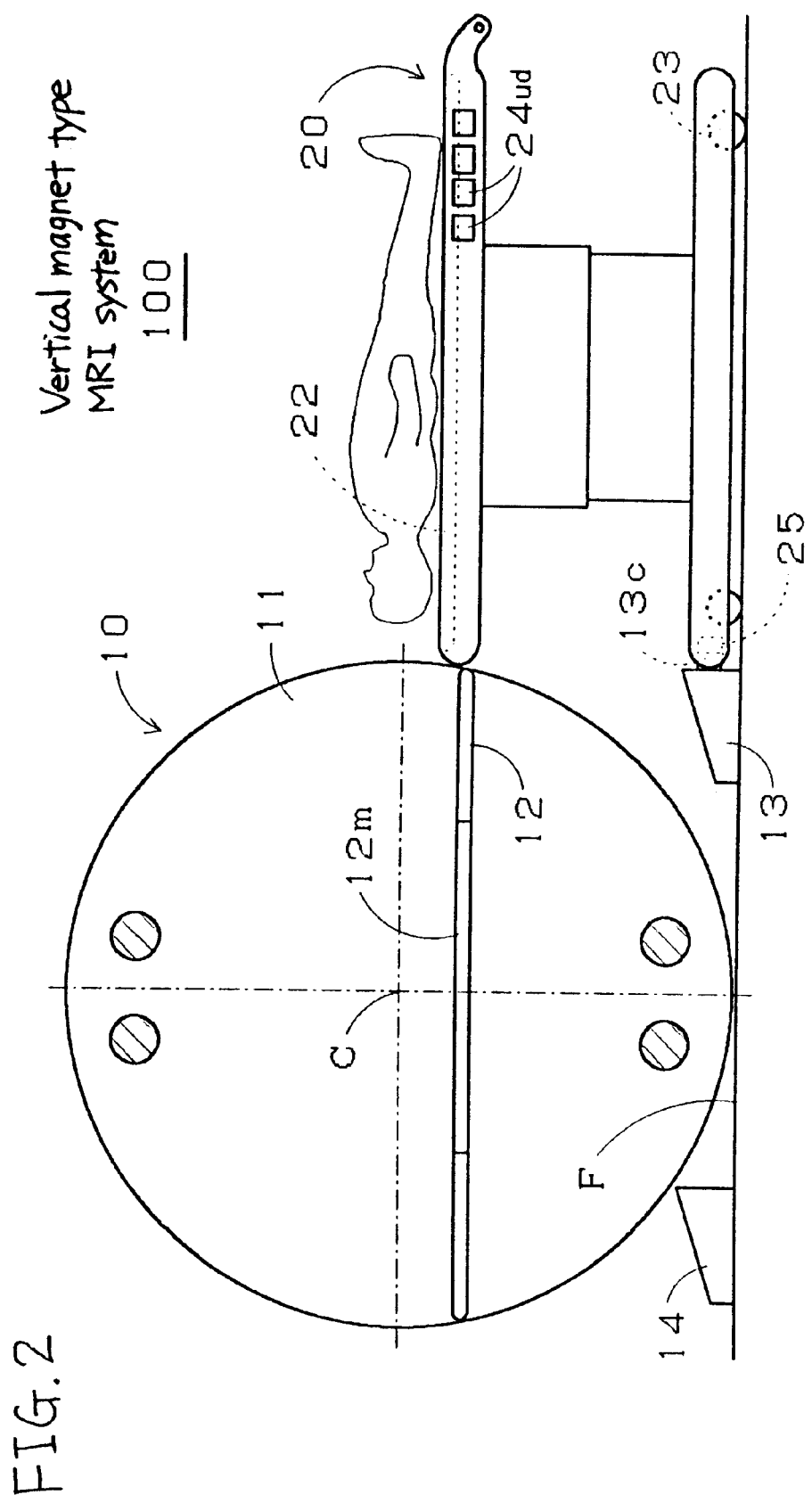
FIG. 2 is a sectional view of the vertical magnet type MRI system of FIG. 1 in a preparatory operation.
Figure 3:
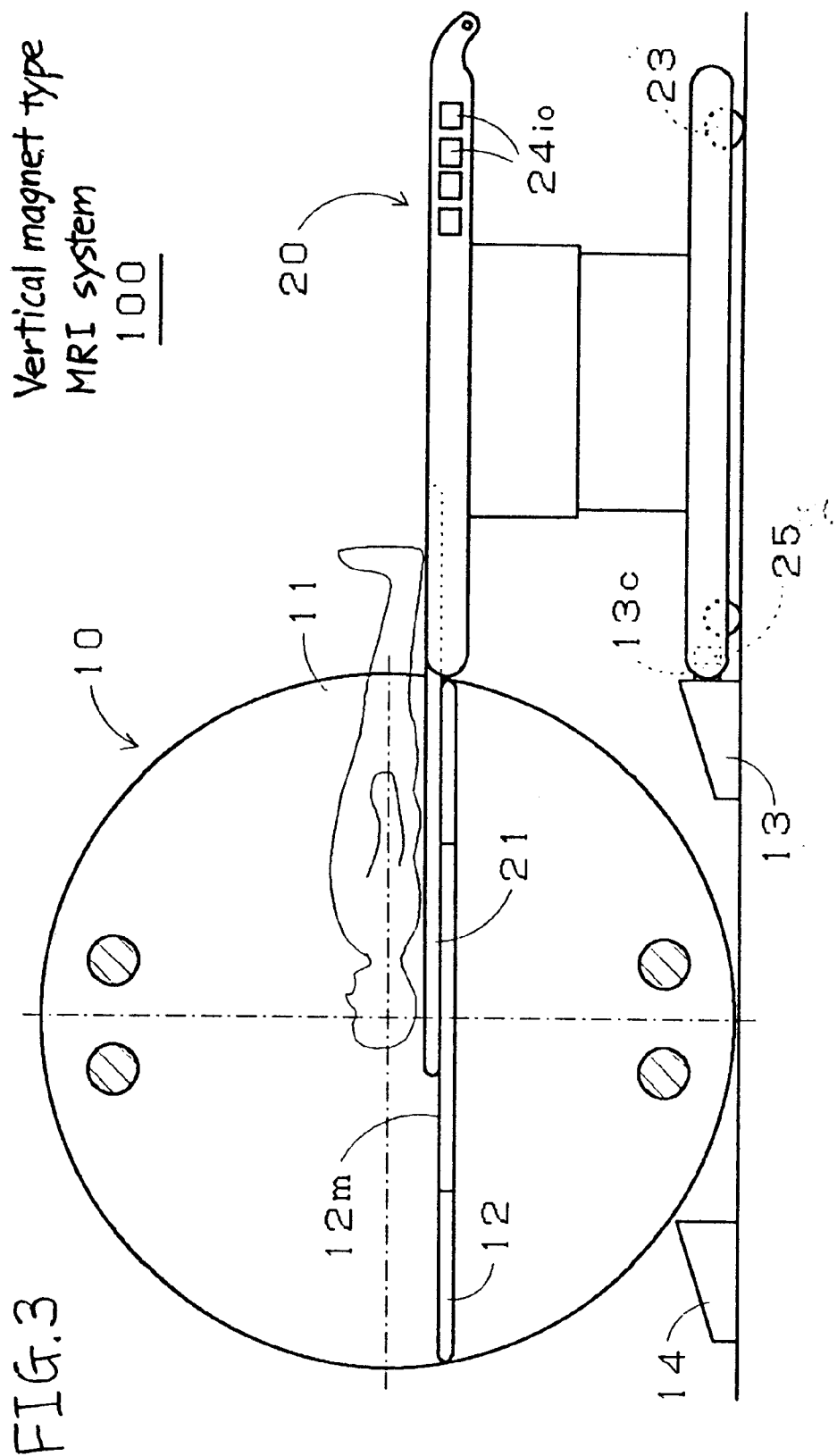
FIG. 3 is a sectional view of the vertical magnet type MRI system of FIG. 1 in an ordinary imaging operation.

FIGS. 2 and 3 are views of assistance in explaining an ordinary imaging operation.

Referring to FIG. 2, the movable table 20 supporting a specimen laid down thereon is carried to the MRI system 100, and is locked in place by the table locking devices 13. In this state, the power feeder connector 13c is connected to the power receiving connector 25 mounted on the movable table 20 to supply power from a gantry to the movable table 20. The up/down buttons 24ud are operated to adjust the height of the table top 21 so that the cradle 22 corresponds to the rails 12.

Then, as shown in FIG. 3, the in/out buttons 24io are operated to move the cradle 22 supporting the lying specimen horizontally away from the table top 21. Twenty rollers are arranged in a row on the lower surface of each of the opposite side parts of the cradle 22. The rollers of the cradle 22 stretched out of the table top 21 roll along the rails 12 and the cradle 22 is supported on the rails 12. Thus, the cradle 21 is placed between the pair of opposite vertical magnets 11 so that a target part of the specimen is located for imaging at a magnet center C.

Figure 4:
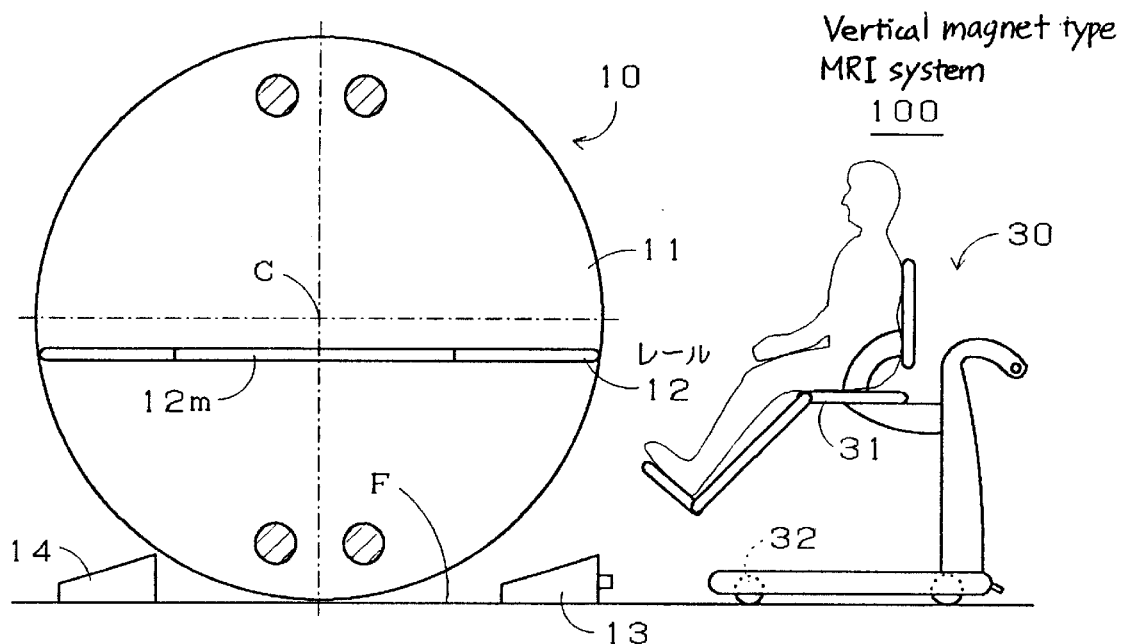
FIG. 4 is a sectional view of the vertical magnet type MRI system of FIG. 1 in a preparatory operation for the joint motion imaging of lumbar vertebrae.
Figure 5:
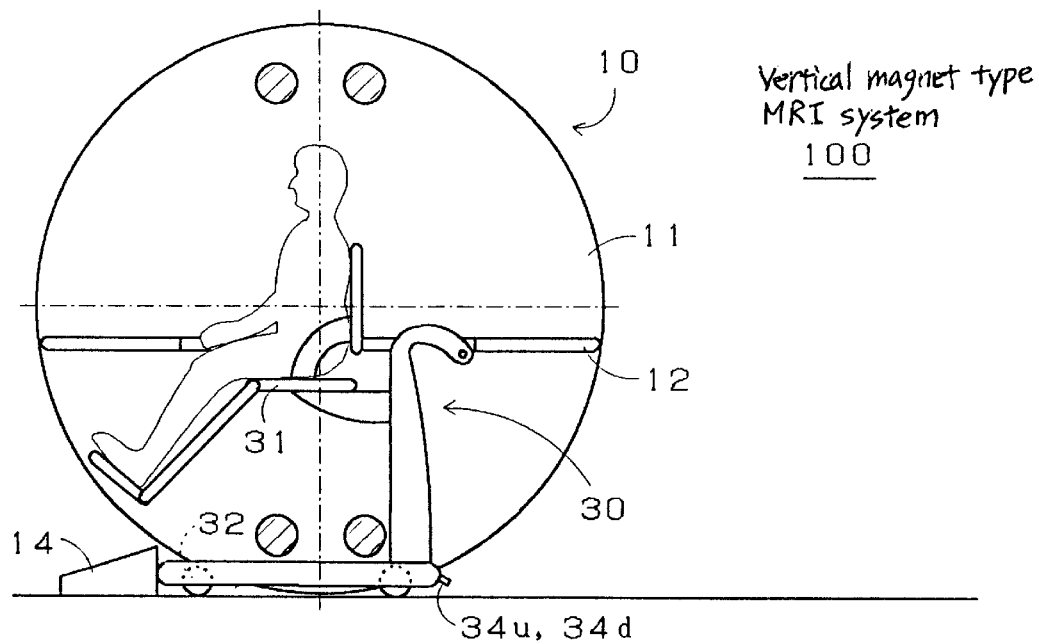
FIG. 5 is a sectional view of the vertical magnet type MRI system of FIG. 1 in a joint motion imaging operation for the joint motion imaging of lumbar vertebrae.
Figure 6:
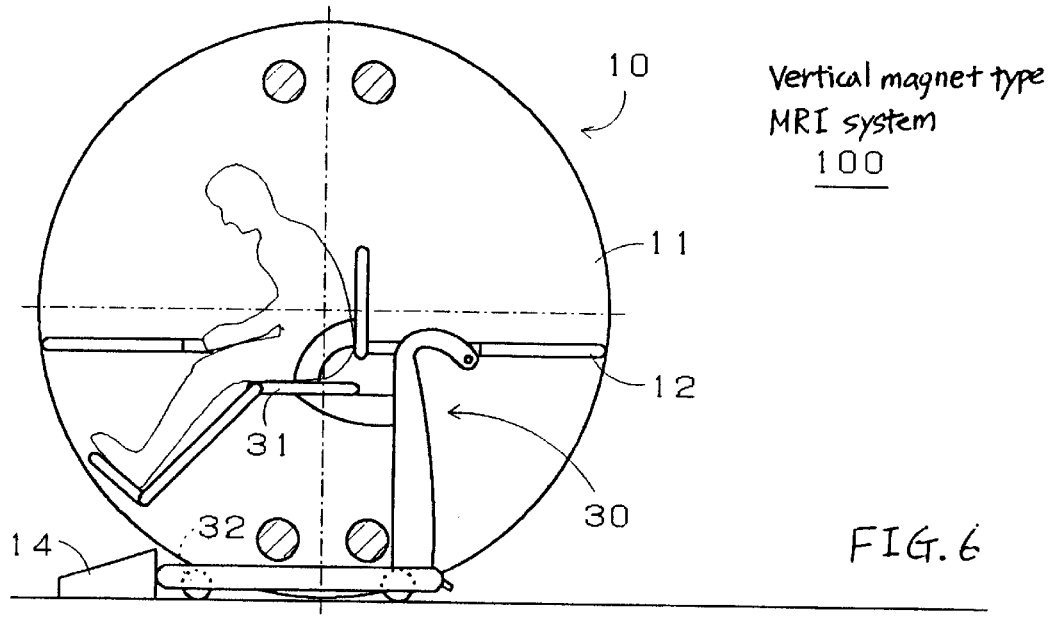
FIG. 6 is a sectional view of the vertical magnet type MRI system of FIG. 1 in another joint motion imaging operation for the joint motion imaging of lumbar vertebrae.

FIGS. 4 to 6 are views of assistance in explaining a joint motion imaging operation for the joint motion imaging of the lumbar vertebrae.

Referring to FIG. 4, the movable chair 30 supporting a specimen in a sitting position thereon is carried to the MRI system 100. The movable chair 30 is placed between the pair of opposite vertical magnets 11 and is locked in place by the chair locking device 14. The raising pedal 34u and the lowering pedal 34d are operated to position target lumbar vertebrae of the specimen at the magnet center C. The specimen is fixedly held for imaging in a position in which the lumbar is not bent.

The movable chair 30, in FIGS. 4–8, comprises a bottom platform, wheels connected to the bottom platform, a vertical standard, shown to the right of the bottom platform, and attached to the bottom platform, a foldable chair, a back plate, extendible leg holder movably connected to the seat, and handle for moving the chair attached to the vertical standard.

As shown in FIG. 6, the specimen is fixed for imaging in a bent position in which the lumbar is bent at a predetermined angle.

The imaging operation is executed for different bent positions of the specimen in which the lumbar is bent in different angles.

Figure 7:
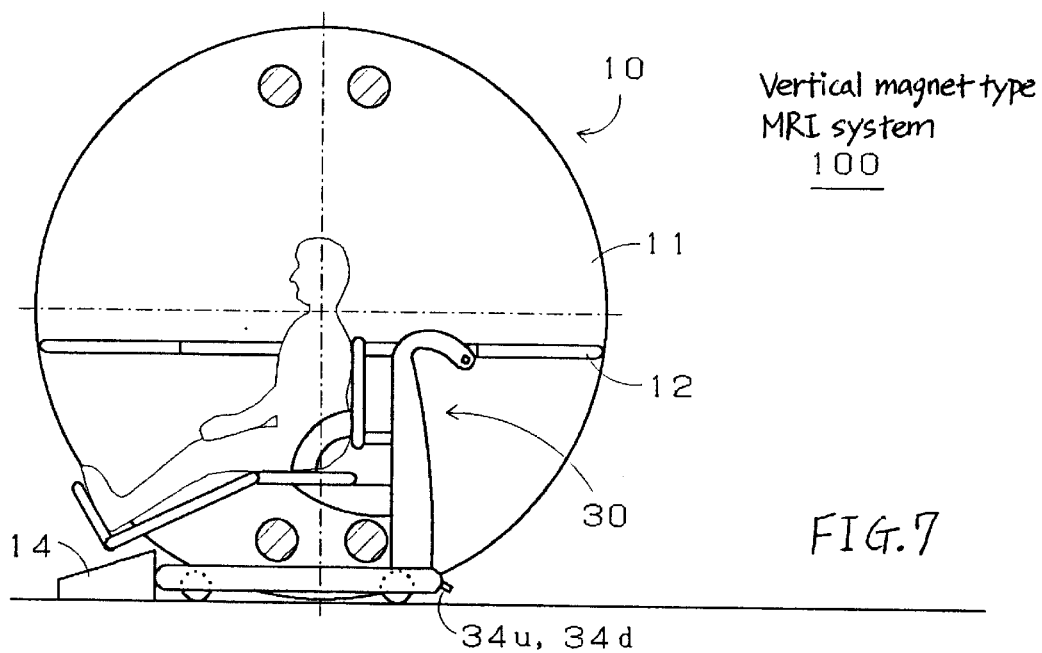
FIG. 7 is a sectional view of the vertical magnet type MRI system of FIG. 1 in a joint motion imaging operation for the joint motion imaging of cervical vertebrae.
Figure 8:
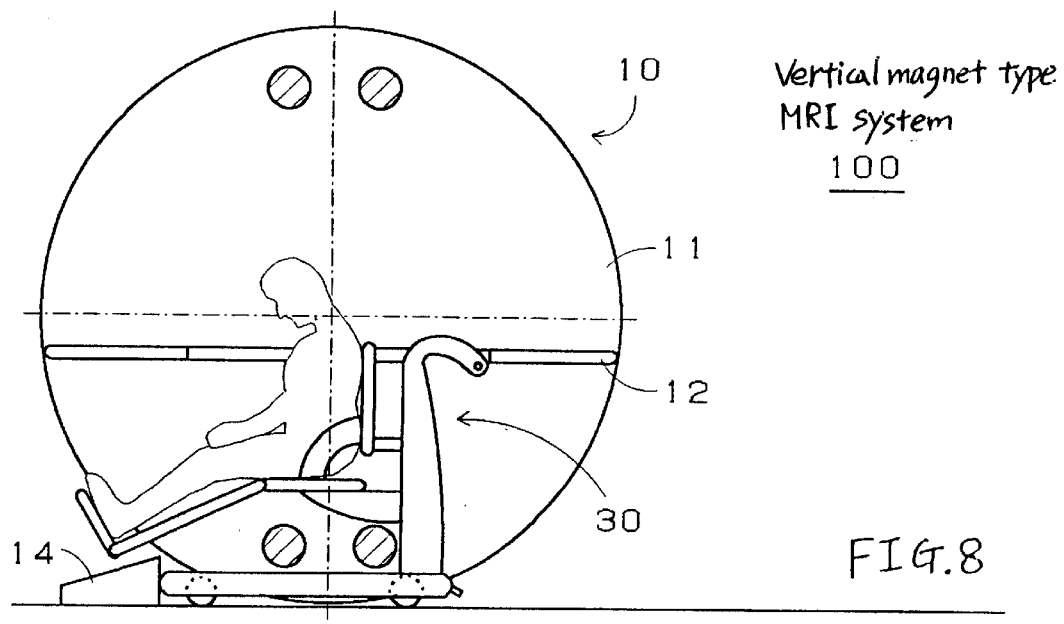
FIG. 8 is a sectional view of the vertical magnet type MRI system of FIG. 1 in another joint motion imaging operation for the joint motion imaging of cervical vertebrae.

FIGS. 7 and 8 are views of assistance in explaining a joint motion imaging operation for the joint motion imaging of cervical vertebrae.

Referring to FIG. 7, the movable chair 30 supporting a specimen in a sitting position thereon is carried to the MRI system 100. The movable chair 30 is placed between the pair of opposite vertical magnets 11 and is locked to the chair locking device 14. The raising pedal 34u and the lowering pedal 34d are operated to position target cervical vertebrae of the specimen at the magnet center C. If the specimen has broad shoulders, the middle sections 12m of the rails 12 are removed, and the imaging operation is executed with the neck held in an upright position.

As shown in FIG. 8, the imaging operation is executed also with the neck held in a bent position.

The imaging operation is executed for different bent positions of the neck in which the neck is bent in different angles.

The movable chair 30 supporting the specimen in a sitting position can be moved to and located at the magnet center C of the vertical magnet type MRI system 100 for satisfactory joint motion imaging after removing the movable table 20 from the vertical magnet unit 10. Since the specimen can be mounted on the movable table 20 or the movable chair 30 at some other place and the movable table 20 or the movable chair 30 supporting the specimen thereon can be carried into the vertical magnet unit 10, work for transferring the specimen is unnecessary and burden on the patient and the technicians can be reduced. Since specimens can quickly be changed, downtime during which the MRI system is stopped can be shortened and the rate of operation of the MRI system 100 can be increased.

Many widely different embodiments of the invention may be constructed without departing from the spirit and the scope of the present invention. It should be understood that the present invention is not limited to the specific embodiments described in the specification, except as defined in the appended claims.

What is claimed is:

1. A patient positioning system comprising, in combination:
    a pair of vertical magnets disposed to have opposite surfaces thereof form a space therebetween and defining a magnetic center thereat and have a bottom position;
    a chair movable into said magnetic center of said space so that said patient seated thereon will be positioned substantially at said magnetic center; and
    rails attached to inside opposing surfaces of said pair of vertical magnets, said rails comprising a removable middle section which is removable so that said chair can be positioned readily between said pair of vertical magnets and within said space.

2. The system of claim 1, further comprising locking means for locking said chair positioned in said space.

3. The system of claim 2, wherein said locking means comprises a blocking device located at said bottom position of said pair of vertical magnets.

4. The system of claim 1, wherein said chair comprises:
    a bottom platform;
    wheels connected to said bottom platform;
    a vertical piece connected to said bottom platform;
    a foldable seat;
    a back plate;
    an extendible leg holder movably connected to said seat; and
    a handle attached to said vertical piece.

5. The system of claim 4, further comprising an upward pedal and a downward pedal disposed under said handle.

6. A patient positioning system comprising, in combination:
    a pair of vertical magnets disposed to have opposite surfaces thereof form a space therebetween and define a magnetic center and a bottom position with a rear end location and a front end location;
    a table movable into said space, said table comprising an extendible cradle for holding horizontally said patient thereon, said table being movable up to and adjacent said pair of vertical magnets, and said cradle being extendible horizontally into said magnetic center of said space;
    a chair movable separately from said table into said space so as to be generally at said magnetic center, said chair being separate from and movable into said space at a different time than when said cradle of said table is extended into said space; and
    a rail disposed on each inner opposite surface of said pair of vertical magnets, said rail being disposed generally at said magnetic center and having a middle section; and wherein, when said table is used, said rail, including said middle section, engages said cradle so that said cradle is extended into and held by said rail in said space; and wherein said middle section is removed when said chair is disposed between said vertical magnets and in said space.

7. The system of claim 6, further comprising:
    first locking means disposed at said bottom position and at said rear end location for stopping said chair so as to accurately position said chair within said space; and
    second locking means disposed at said bottom position and at said front end location for stopping said table so that said cradle is accurately positioned within said space.

8. The system of claim 7, wherein said second locking means comprises an electrical outlet for supplying electric power.

9. A patient positioning system comprising in combination:
    a pair of vertical magnets disposed to have opposite vertical surfaces thereof form a space therebetween and define a magnetic center and a bottom position with a rear end location and a front end location;
    a table movable into said space and up to and adjacent said pair of vertical magnets, said table comprising:
        an extendible cradle for holding said patient horizontally thereon and being movable horizontally into said magnetic center of said space so that said patient is generally at said magnetic center;
        a lower platform;
        wheels connected to said lower platform to horizontally move said table;
        an adjustable vertical support means for adjusting vertical location of said cradle to be generally at said magnetic center of said space;
        an upper platform connected to a top of said adjustable vertical support means, said extendible cradle being disposed on top of said upper platform;
        a handle disposed at one end of said upper platform to enable an operator to horizontally move said table; and
        control means for controlling vertical movement of said vertical support means and horizontal movement of said cradle;
        a rail disposed on each inner surface of said pair of vertical magnets and at generally said magnetic center and engagable with said cradle; and
    locking means disposed at said bottom position and at said front end location so that when said table is moved to said pair of vertical magnets, said lower platform is stopped by said locking means so that accurate placement of said patient on said cradle will take place, and wherein after locking, an operator manipulates said control means to accurately adjust vertical and horizontal positions of said cradle and insert said cradle into said space at generally said magnetic center.

10. The system of claim 9, wherein said control means comprises an electric motor, and wherein a line outlet for electric power is provided at said front end location of said bottom position.

* * * * *